United States Patent [19]

Thorsett et al.

[11] Patent Number: 4,609,742
[45] Date of Patent: Sep. 2, 1986

[54] DIFFICOL, INTERMEDIATE IN ANTIBIOTIC PREPARATION

[75] Inventors: Eugene D. Thorsett, Fanwood; Joanne M. Williamson, Cranford; Kenneth E. Wilson, Westfield, all of N.J.

[73] Assignee: Merck & Co., Inc., Rahway, N.Y.

[21] Appl. No.: 697,806

[22] Filed: Feb. 4, 1985

[51] Int. Cl.⁴ .......................................... C07D 313/00
[52] U.S. Cl. ..................................... 549/271; 435/124
[58] Field of Search ......................................... 549/271

[56] References Cited
FOREIGN PATENT DOCUMENTS
84106408.2 12/1984 European Pat. Off. .

Primary Examiner—Jane T. Fan
Attorney, Agent, or Firm—Hesna J. Pfeiffer; Thomas E. Arther

[57] ABSTRACT

The subject disclosure discloses a chemical intermediate in antibiotic synthesis of the structure:

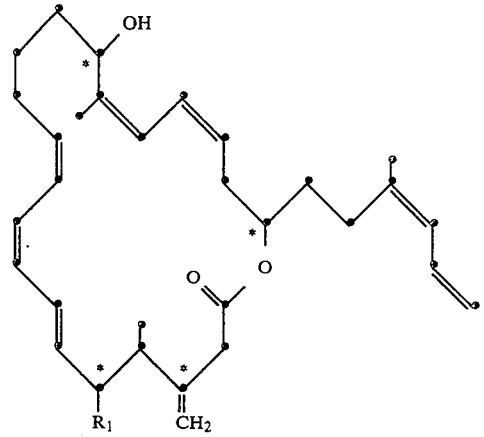

wherein $R_1$ is H or OH and the asterisks indicate asymmetric carbon atoms. Compounds of this type may be obtained by fermentation with a strain of *B. subtilis* under aerobic conditions. Compounds of the above structure are biologically inactive but are converted by phosphorylation of the hydroxyl group to produce compounds of the structure:

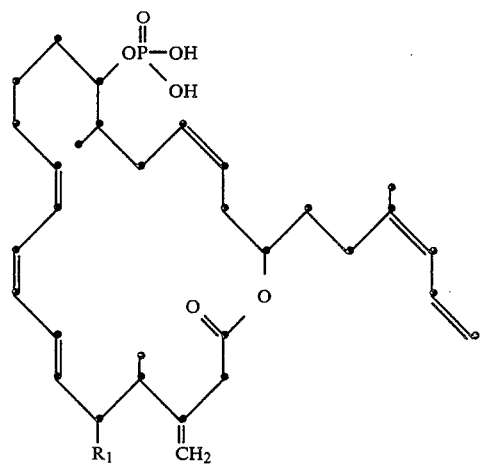

wherein $R_1$ is H or OH, which are useful antibacterial substances having a broad spectrum of antibacterial activity.

3 Claims, No Drawings

DIFFICOL, INTERMEDIATE IN ANTIBIOTIC PREPARATION

BACKGROUND OF THE INVENTION

The present invention relates to a novel fermentation product referred to herein as difficol or oxydifficol and to a process for preparing, isolating and purifying said compounds. The term difficol refers to the compound of Formula I hereinbelow wherein $R_1$ is hydrogen and the term oxydifficol refers to the compound of Formula I wherein R is hydroxy. The novel fermentation products are prepared by microbiological cultivation of *Bacillus subtilis* MB 3575 and MB 4488 deposited with the American Type Culture Collection, Rockville, Md. under the designation ATCC 39374 and 39320 respectively.

The novel fermentation products are useful as intermediates in the production of the broad spectrum antibiotics difficidin, oxydifficidin. These broad spectrum antibiotics and method of preparing them are disclosed in EPO Application No. 84106408.2, Publication No. 0128505—published Dec. 14, 1984. However, it is noted that this published application contains no suggestion that difficol is present in or recoverable from the cultivation of *Bacillus subtilis* microorganisms.

DETAILED DESCRIPTION OF THE INVENTION

In accordance with the present invention there is provided a compound of Formula I hereinbelow useful as an intermediate in the preparation of broad spectrum antibiotics of the difficidin and oxydifficidin type.

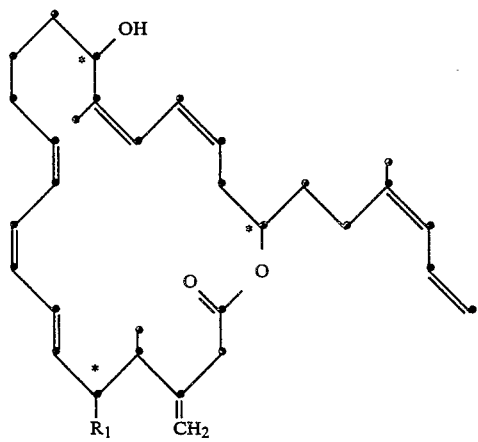

wherein $R_1$ is hydrogen or hydroxy.

Difficol is represented by the above formula when $R_1$ is hydrogen and oxydifficol is represented by the above formula when $R_1$ is hydroxy. It is unexpected to find that these macrocyclic alcohols are biologically inactive but when the hydroxyl group is phosphorylated to produce the corresponding difficidin or oxydifficidin, the resulting compounds are highly active broad spectrum antibacterials of the formula:

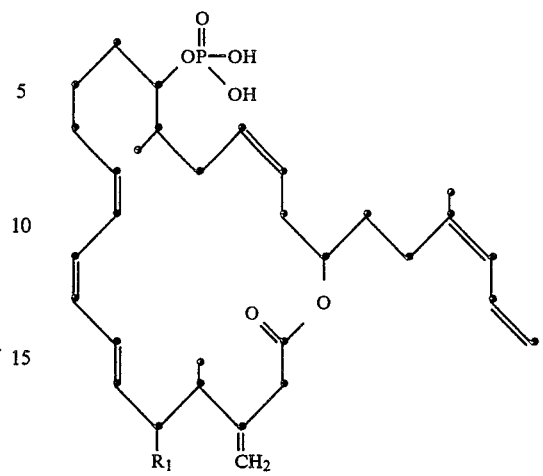

wherein $R_1$ is H or OH.

Difficol and oxydifficol may be prepared by microbiological cultivation of *Bacillus subtilis*, MB 3575 and MB 4488 deposited with the American Type Culture Collection, Rockville, Md., from which it is available without restriction under the accession numbers ATCC 39374 and 39320, respectively.

The Bacillus, or its variants and mutants may be cultivated in accordance with well known microbiological processes, either on agar slant tubes, or under submerged conditions in Erlenmeyer flasks or fermentors, utilizing nutrient media or nutrient solutions generally employed for cultivating microorganisms.

In the present invention, difficol and its hydroxy derivative are produced during cultivation of the microorganism, for example, *Bacillus subtilis* ATCC 39320 at a temperature of about 28° C., under aerobic conditions. The composition of the nutrient medium may be varied over a wide range. The essential assimilable nutrient ingredients are; a carbon source, a nitrogen source, a source of inorganic elements including phosphorus, sulfur, magnesium, potassium, calcium and chlorine. Cultivation is most productive under neutral pH conditions, preferably from about 6.0 to 7.0.

Typical sources of carbon include glucose, dextrin, starches, glycerol and the like. Typical nitrogen sources include vegetable meals (soy, cottonseed, corn, etc.), meat flours or animal peptones, distillers solubles, casamino acids, yeast cells, various hydrolysates (casein, yeast, soybean, etc.), yeast nucleic acids and amino acids.

Mineral salts such as the chlorides, nitrates, sulfates, carbonates and phosphates of sodium, potassium, ammonium, magnesium and calcium provide a source of essential inorganic elements. The nutritive medium may also contain a number of trace elements such as iron, copper, manganese, zinc and cobalt.

If excessive foaming is encountered during the cultivation, antifoaming agents such as vegetable oils, lard oil and polypropylene glycol may be added to the fermentation medium prior to, or during the course of the fermentation. The maximum yield of difficol can be achieved within from about 20 to 120 hours, and is culture dependent. The inoculum for the fermentation can be provided from suspensions, slants, frozen cells or freeze-dried preparations.

In addition to the conventional cultivation processes described above, there may also be employed continuous processes, such as that described in *Methods in Microbiology*, Vol. 2, Academic Press, London-New York, 1970, pp. 259-328. In such systems the bacillus can be maintained for extended periods of time in a steady state without spontaneous mutations or other degenerations becoming evident.

It is to be understood that for the production of difficol and oxydifficol, the present invention is not limited to the use of *Bacillus subtilis* ATCC 39374 or 39320. It is especially desired and intended to include the use of natural or artificial mutants produced from the described organisms, or other variants of *Bacillus subtilis* ATCC 39374 or 39320 as far as they can produce difficol and oxydifficol. The artificial production of mutant *Bacillus subtilis* may be achieved by a conventional operation such as X-ray or ultraviolet (UV) radiation, or by the use of chemical mutagens such as; nitrogen mustards, nitrosoguanidine, camphor and the like, or by means of recombinant DNA technology.

In another aspect of the present invention it has been found that the yield of oxydifficol is greatly increased by a two-step procedure which involves (1) cultivating strain MB 3575 preferably for a period of 5 days and (2) following the fermentation, adjusting the pH to 8.3-8.5 with buffer solution and adding magnesium chloride (0.2 M). The resulting mixture is then agitated for a period of about 24 hours at room temperature or about 25° C. The yield of oxydifficol product ranges from 40-60 µg/ml of treated fermentation broth which represents a substantial increase in yield compared to that obtained by extraction from the harvested broth without any subsequent treatment.

MORPHOLOGICAL AND PHYSIOLOGICAL CHARACTERISTICS OF *Bacillus subtilis* ATCC 39320

The morphological and physiological properties of ATCC 39320 are as follows:

Morphology: gram positive, non-vacuolated vegetative rods with rounded ends; average size 0.9×2.3-3.6µ; occurring singly. Rods are motile. Spores are produced under aerobic conditions. Spores are 0.5×1.0µ (average size), oval to cylindrical, predominantly central, sporangia not swollen.

Colonial appearance: flat, round with irregular edge, surface dull, edge becoming opaque as colony ages. Dull, wrinkled entire pellicle on surface of broth. No pigmentation on trypticase soy agar. Growth at 28° C., 37° C., no growth at 60° C.

Positive reactions: Catalase, Voges-Proskauer, gelatin, nitrate reduction, utilization of citrate, acid from glucose, arabinose, mannitol, xylose, sorbitol and sucrose, hydrolysis of starch.

Negative reactions: urease, indole, utilization of propionate, arginine dihydrolase, acid from rhamnose and mellibiose, no growth in anaerobic agar (stabs or plates incubated in anaerobic jars), no growth in glucose broth or nitrate broth under anaerobic conditions.

Comparison with culture descriptions in Bergey's *Manual of Determinative Bacteriology*, Eighth Edition, Williams & Wikins, 1974, and Gordon, R. E., Haynes, W. C. and Pang, C. H. (1973), The Genus Bacillus, Agriculture Monograph No. 427, U.S. Department of Agriculture, Washington, D.C., indicate that MB 4488/ATCC 39320 is a strain of known species *Bacillus subtilis*.

MORPHOLOGICAL AND PHYSIOLOGICAL CHARACTERISTICS OF *Bacillus subtilis* ATCC 39374

The morphological and physiological properties of ATCC 39374 are the same as those indicated above for ATCC 39320, except with respect to the appearance of the colonies of the microorganism, which are as follows:

Colonial appearance:
  At 24 hours, raised, round, mucoid. As colony ages, edge becomes dry, opaque and irregular. Central mucoid area continues to dry, becoming opaque and wrinkled.
  Dull, wrinkled entire pellicle on surface of broth. No pigmentation on trypticase soy agar. Growth at 28° C., 37° C., no growth at 60° C.

PRODUCTION OF DIFFICOL AND OXYDIFFICOL

A. A process for preparing difficol and its derivatives, involves the cultivation of microorganisms which belong to the strain of *Bacillus subtilis* ATCC 39320 at a temperature ranging from 20° to 40° C. for from 24 to 120 hours by means of an aqueous nutrient solution which contains a source of carbon, a source of nitrogen, nutrient salts and trace elements, until the nutrient solution contains difficol and oxydifficol after which the compounds are isolated from the culture. Isolation of the compounds is accomplished by extraction of the whole broth (supernatant and cells) with a solvent such as hexane followed by chromatographic purification.

In an alternative method difficol or oxydifficol is produced by treatment of difficidin or oxydifficidin using an alkaline phosphatase enzyme which is present in most living cells and for economic reasons is readily isolated from calf intestinal mucosa. In addition oxydifficol may be obtained directly from fermentation broth containing oxydifficidin using the alkaline phosphatase enzyme produced in situ by fermentation.

EXAMPLE 1

Difficol and Oxydifficol from Fermentation Culture Media are Prepared as Follows:

| Component | Seed Medium: 1. HSM-1 Amount (g/l) |
|---|---|
| Yeast Extract | 1.0 |
| Malt Extract | 1.0 |
| Beef Extract | 1.0 |
| Trypticase Peptone | 2.5 |
| Trypticase Soy | 0.1 |
| Glucose | 5.0 |
| Soy Bean Oil | 0.1 |
| Corn Steep Liquor | 0.5 |
| Calcium Carbonate | 10.0 |

-continued

| Seed Medium: 1. HSM-1 | |
|---|---|
| Component | Amount (g/l) |
| Sucrose | 10.0 |
| Soy Bean Flour | 10.0 |
| Soluble Starch | 10.0 |

The medium is prepared with distilled water. No pH adjustment is required. The medium is dispensed, 54 ml/250 ml three-baffle erlenmeyer flask. The flasks are sealed with cotton plugs and sterilized at 121° C. for 20 minutes.

| Fermentation Media: 1. KRC | |
|---|---|
| Component | Amount (g/l) |
| Dextrin | 40.0 |
| Solulac | 7.0 |
| Yeast Extract | 5.0 |
| $CoCl_2.6H_2O$ | 0.10 |

The medium is prepared with distilled water. The pre-sterile pH is adjusted to 7.3 by the addition of NaOH. The medium is dispensed, 44 ml/250 ml plain erlenmeyer flask. The flasks are sealed with cotton plugs and sterilized at 121° C. for 20 minutes.

| 2. Synthetic | |
|---|---|
| Component | Amount (g/l) |
| Dextrin | 50.0 |
| Diammonium citrate | 3.0 |
| $MgSO_4.7H_2O$ | 1.5 |
| Potassium phosphate dibasic | 0.15 |
| $CoCl_2.6H_2O$ | 0.10 |
| MOPSO buffer* | 11.3 |
| Trace elements solution | 5.0 ml/l |

*MOPSO is 3-(N—morpholino)-2-hydroxypropanesulfonic acid

The medium is prepared with distilled water. To improve cell growth, yeast extract (10 g/l) may also be added. The pre-sterile pH is adjusted to 6.7 by the addition of NaOH. The medium is dispensed, 44 ml/250 ml plain erlenmeyer flask. The flasks are sealed with cotton plugs and sterilized at 121° C. for 20 minutes.

| 2a. Trace Elements Solution | |
|---|---|
| Component | Amount (g/l) |
| $MgSO_4.7H_2O$ | 61.0 |
| $CaCO_3$ | 2.0 |
| $FeCl_3.6H_2O$ | 5.4 |
| $ZnSO_4.7H_2O$ | 1.4 |
| $MnSO_4.H_2O$ | 1.1 |
| $CuSO_4.5H_2O$ | 0.25 |
| $CoCl_2.6H_2O$ | 0.28 |
| $H_3Bo_3$ | 0.062 |
| $Na_2MoO_4.2H_2O$ | 0.49 |

The components are dissolved in 950 ml of distilled water. Concentrated HCl (50 ml) is then added. the solution is filtered through an 0.45 μm filter after preparation.

| 3. PD Medium | |
|---|---|
| Component | Amount (g/l) |
| Dextrin | 80.0 |
| Proflo | 20.0 |
| Potassium phosphate dibasic | 0.5 |
| Lactic acid (85%) | 1.8 |
| Polypropyleneglycol-2000 (Dow) | 1.0 ml/l |

The medium is prepared with distilled water. The pre-sterile pH is adjusted to 7.3 by the addition of NaOH. The medium is dispensed, 44 ml/250 ml plain erlenmeyer flask. The flasks are sealed with cotton plugs and sterilized at 121° C. for 20 minutes.

The fermentation is carried out as described below:

1. Seed Preparation

HSM-1 seed medium is inoculated with any suitable source (spores or vegetative cells) of either MB 4488 or MB 3575. The culture is grown at 27° C. and 220 rpm for 12 hours.

2. Production Phase

A seed culture prepared as described above is used to inoculate fermentation media as follows:

| Medium | Amount Seed/Flask (ml) |
|---|---|
| KRC | 2.0 |
| Synthetic | 1.0 |
| PD | 2.0 |

The production flasks are incubated at 27° C. and 220 rpm from 22-120 hours as desired.

A 125 ml portion of fermentation broth, preferably from KRC or synthetic medium, is extracted with hexane (2×100 ml). The hexane extracts are combined, dried and concentrated. The residue is purified by reverse phase chromatography. For example, under the following conditions oxydifficol had a retention time of 5.1 minutes and difficol had a retention time of 11.4 minutes.

Column: Waters μ-Bondapak ®, C-18 reverse phase, 4.5×25 cm.

Eluent: Methanol (84):0.01M pH 7 potassium phosphate (16).

Temp.: 26° C.

Flow: 1.3 ml/minute.

Detection: absorbance at 275 nm.

The appropriate eluate fractions are combined and concentrated. The concentrated solutions are extracted with ethyl acetate. The ethyl acetate extracts are concentrated to afford difficol and oxydifficol.

Alternatively, the broth extracts may be concentrated and the residue purified over silica gel using hexane:ethyl acetate mixtures as eluent.

EXAMPLE 2

Preparation of Difficidin from Difficol

To a solution of 44 mg difficol in 1.5 ml methylene chloride is added 31.5 mg 1,2-dibromo-1-phenylethylphosphonic acid. The suspension is stirred at room temperature while 35 μl diisopropylethylamine is added. A clear solution results. After 16 hours at room temperature the reaction is concentrated and the residue triturated with hexane. The hexane solution is discarded and the remaining residue is dissolved in methanol. Purification of the methanol soluble portion by reverse-phase chromatography using methanol-potassium phosphate buffer (0.01M, pH 7) as eluent affords difficidin. The synthetic product is identical by chromatographic and spectral analysis with difficidin isolated from fermentation sources.

EXAMPLE 3

Preparation of Oxydifficidin from Oxydifficol

Oxydifficol affords oxydifficidin using the conditions described in Example 2.

EXAMPLE 4

Preparation of Difficol from Difficidin

A solution of 500 mg of difficidin in 14 ml methanol and 77 ml of 0.1 M sodium glycinate (pH 9.5) is treated with about 5000 units of alkaline phosphatase (from calf intestinal mucosa). The reaction is stirred under nitrogen at 25° C. for 24 hours. Sodium chloride is then added and the reaction mixture is extracted with ethyl acetate (2×50 ml). The extracts are dried ($Na_2SO_4$) and concentrated to an oil which is chromatographed on a C-8 reverse phase column using methanol (95):0.01M potassium phosphate, pH 7 (5) as eluent. The fractions containing difficol are concentrated and the residue taken up in ethyl acetate. The resulting solution is dried and reconcentrated to an oil which is chromatographed over silica gel using hexane (4):ethyl acetate (1) as eluent. The purified difficol is obtained as a clear oil. TLC (silica gel, 7 hexane:3 ethyl acetate): Rf=0.6.

Spectral data:

NMR ($CDCl_3$, 200 MHz): δ1.08 (d, J=6 Hz, 3H); 1.37–1.95 (m, 8H); 1.82 (s, 3H); 1.86 (s, 3H); 2.04–2.78 (m, 8H); 3.05 (d of d, J=12 Hz, 2H); 4.78 (broad d, 1H); 4.88–5.27 (m), 5.3–5.5 (d of t), 5.63–5.9 (m), 5.9–6.35 (m), 6.35–6.70 (m), 4.88–6.70 (total 16H).

Mass Spectrum: $M^+=464$.

UV Spectrum (Methanol): 282 nm, 272 nm, 261 nm, 234 nm.

EXAMPLE 5

Preparation of Oxydifficol from Oxydifficidin

A solution of 500 mg oxydifficidin in 14 ml methanol and 77 ml 0.1 M sodium glycinate (pH 8.5) is treated with about 5000 units of alkaline phosphatase (from calf intestinal mucosa). The reaction is stirred at 25° C. and the pH is maintained between 8.5 and 8.6 by addition of 2.14 M potassium hydroxide solution. After 2.5 hours sodium chloride is added to the reaction and it is extracted with ethyl acetate (2×50 ml). Purification is as described above for difficol.

Spectral data:

NMR ($CDCl_3$, 400 MHz): δ1.1 (d, J=8 Hz); 1.18–1.80 (m); 1.68 (s); 1.74 (s); 1.86–2.56 (m); 2.98 (d); 3.15 (d); 4.20 (broad d); 4.70 (broad d); 4.8–5.3 (m); 5.42 (m); 5.74–5.84 (m); 5.9–6.18 (m); 6.25 (t); 6.4–6.58 (m); 6.75 (t).

Mass Spectrum: $M^+=480$.

UV Spectrum (Methanol): 282 nm; 273 nm; 261 nm; 234 nm.

What is claimed is:

1. A compound of the formula:

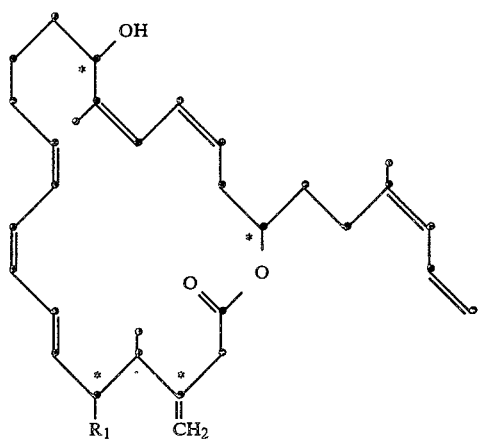

wherein $R_1$ is hydrogen or hydroxy.

2. A compound according to claim 1 wherein $R_1$ is hydroxy.

3. A compound according to claim 1 wherein $R_1$ is hydrogen.

* * * * *